United States Patent

Nakao

[11] Patent Number: 5,573,546
[45] Date of Patent: Nov. 12, 1996

[54] BIOPSY EJECTING FORCEPS

[76] Inventor: Naomi L. Nakao, 303 East 57th St., New York, N.Y. 10022

[21] Appl. No.: 399,453
[22] Filed: Mar. 7, 1995
[51] Int. Cl.$^6$ .................................................. A61B 17/28
[52] U.S. Cl. ......................... 606/205; 606/207; 606/208; 606/170; 128/751
[58] Field of Search .................................... 606/205, 206, 606/207, 208, 170; 128/751

[56] References Cited

U.S. PATENT DOCUMENTS

| | | | |
|---|---|---|---|
| 4,721,116 | 1/1988 | Schintgen et al. | 128/751 |
| 4,763,668 | 8/1988 | Macek et al. | 128/751 |
| 4,785,825 | 11/1988 | Romaniuk et al. | 128/751 |
| 5,082,000 | 1/1992 | Picha et al. | 128/751 |
| 5,172,700 | 12/1992 | Bencini et al. | 128/751 |
| 5,373,854 | 12/1994 | Kolozsi | 128/749 |

Primary Examiner—Michael Powell Buiz
Assistant Examiner—Mark S. Leonardo
Attorney, Agent, or Firm—Abelman, Frayne & Schwab

[57] ABSTRACT

An improved biopsy forceps for retrieving a tissue sample from an internal organ includes device for ejecting a tissue sample from the cups after the sample is retrieved from the internal organ. The improved biopsy forceps has scissor links for operating the cups, and plungers rigidly attached to the scissor links. The plungers protrude through apertures in the cups when the cups are fully opened, ejecting the tissue sample. Alternatively, the forceps have pushing members positioned inside of the cups and attached to the distal end of an actuating wire. The ejection device is actuated from the proximal end of the forceps by sliding the wire. A latch mechanism can be provided on the proximal end to selectively prevent actuation.

15 Claims, 9 Drawing Sheets

BIOPSY EJECTING FORCEPS

FIELD OF THE INVENTION

The invention relates to flexible biopsy forceps used in conjunction with an endoscope and rigid forceps used with a laproscope for retrieval of a tissue sample from the interior of a patient's body.

BACKGROUND OF THE INVENTION

Flexible biopsy forceps are used in conjunction with a fiberoptic endoscope as follows: the endoscope is inserted into the stomach, colon or other hollow organ of the patient's body, an abnormality is visualized, and the flexible biopsy forceps is introduced through the biopsy channel of the endoscope. The distal end of the biopsy forceps is comprised of two opposed sharp-edged cups that are operably attached by means of pivot arms to a wire passing on the interior of a flexible cable. Actuation means operably connected to the proximal ends of the flexible cable and wire cause the cups to move between an open and closed position.

When the forceps' distal end is properly positioned at the sampling site, the cups are moved to the open position, advanced to contact the tissue and then closed on the tissue, grasping and severing a sample of tissue that is held within the closed cups while the forceps is withdrawn from the patient.

The rigid forceps are employed in conjunction with the laproscopic procedure in a similar manner. With both types of the device, after the forceps has been removed from the endoscope, the tissue sample must then be placed into an appropriate receptacle that contains a preservative (e.g., formalin). In many instances, it is difficult to remove the sample from the forceps cup. Each of the cups of the biopsy forceps is provided with a small opening, or hole, in the central region to receive the end of a needle or other pointed implement. The doctor or assisting personnel will typically use a needle to pry the tissue out of the cup, or otherwise dislodge the sample from the distal end of the forceps. This task is difficult and cumbersome in itself, and dangerous since there are occasions in which medical personnel have been stuck by the needle. If the patient is infected with the HIV virus, or hepatitis, or another contagious disease, the assistant will be infected as well. An additional risk to the medical personnel from an infectious sample is posed by the sharp cutting edges of the cups themselves.

It is therefore an object of the invention to provide a modified biopsy forceps that will eject the biopsy sample from the distal end of the forceps into a convenient receptacle by manipulation of interconnected control means at the proximal end of the forceps.

It is another object of this invention to provide an improved biopsy forceps having means for ejecting the tissue sample that can be incorporated into forceps of current construct with a minimal change in design.

Another object of the invention to provide tissue sample ejecting biopsy forceps that are easy to use and that operate in the same manner to remove tissue samples as the prior art forceps.

A further object of the invention is to provide an improved biopsy forceps from which the tissue sample can be safely ejected without having the medical personnel directly contact or manipulate the distal end of the forceps.

These and other objects are met by the improved biopsy forceps that are described below.

BRIEF DESCRIPTION OF THE INVENTION

As broadly contemplated, the biopsy ejecting forceps of the invention comprises tissue sample ejection means located at the distal end of the forceps that moves in relation to the cups to contact the sample inside of the cups and dislodge it as the cups are moved beyond the open position used during the tissue collection procedure. This is done by control means located at the proximal end of the forceps.

In one preferred embodiment the tissue sample ejecting means is located outside of, and proximally displaced from the cups while the cups are closed and partially opened to sever the tissue sample, and pivotally moves to pass through openings in the central section of each of the cups to contact and dislodge the sample when the cups are moved to a more fully opened position.

In another preferred embodiment, the tissue sample ejecting means is located between the cups at their proximal ends, and moves axially after the cups are opened to contact and dislodge the sample.

In each embodiment, the sample ejecting means is remotely activated by control means located at the proximal end of the forceps by the axial movement of at least one wire located in the flexible cable that is secured to the distal and proximal ends the forceps.

DETAILED DESCRIPTION OF THE INVENTION

Figure 1:
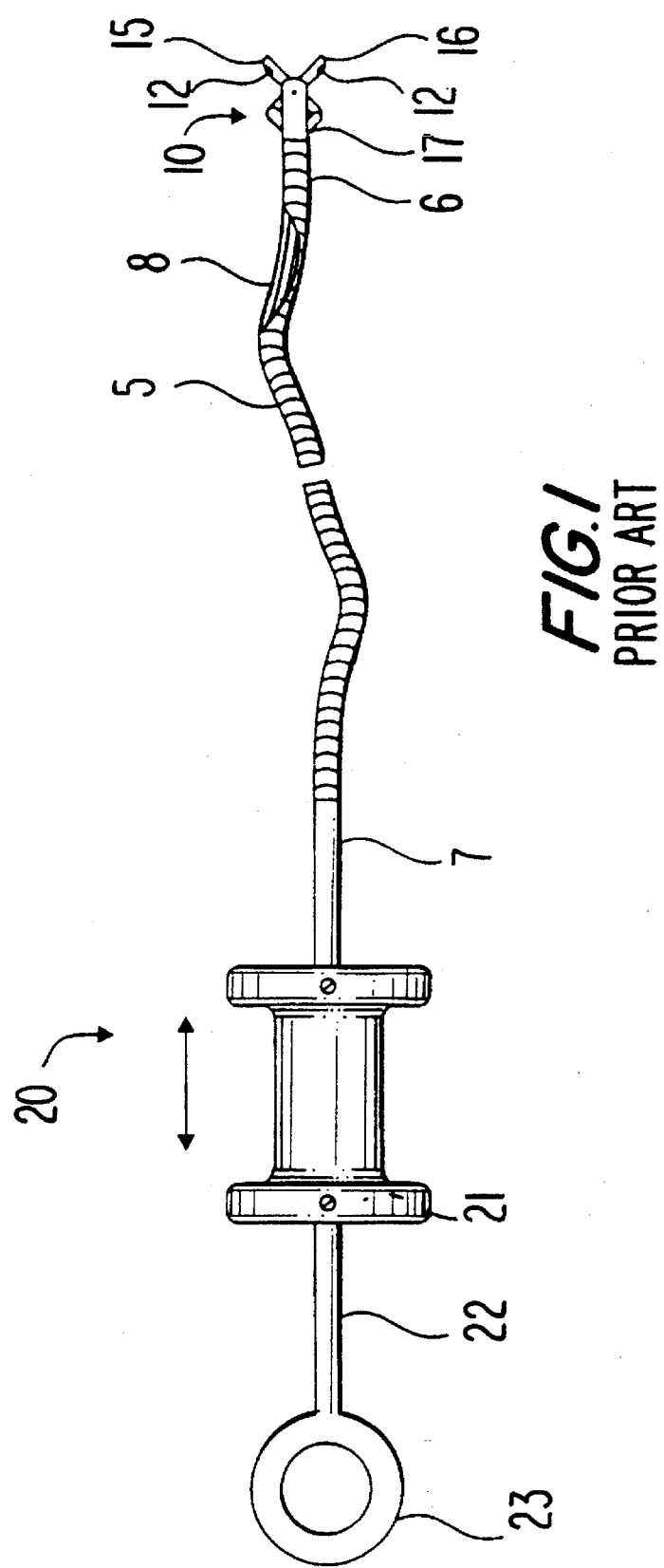
FIG. 1 is a partial cut-away view of a conventional biopsy forceps of the prior art.

A conventional biopsy forceps 1 known in the art is shown in FIG. 1. The forceps comprises a hollow, flexible cable 5 having a distal end 6 and a proximal end 7. An actuating wire 8 is slidably disposed within the cable and extends from the distal to the proximal ends of the cable. At the distal end of the cable is a tissue sample collection means 10, typically comprising two opposing cups 15 and 16 pivotally attached to a clevis 17 depending from the cable 5. The cups are operably attached to the wire 8, so that sliding the wire distally opens the cups, and sliding the wire proximally closes the cups.

At the proximal end 7 of the cable 5 is an actuation means 20, typically comprising a spool 21 slidably mounted on a shaft 22. The shaft has a finger or thumb grip 23 depending from its proximal end. The cable 5 is mounted to the shaft 22. The wire 8 is operably attached to the spool 21, so that an axial sliding movement of the spool 21 on the shaft 22 will produce a similar movement of the wire 8 within the cable 5, thus opening and closing the cups 15 and 16. The opposing edges of the cups are sharpened. When the biopsy forceps is in use, a surgeon opens and closes the cups 15 and 16 by sliding the spool 21 on the shaft 22. The sharpened edges of the cup engage the tissue and sever a small sample which is retained in the cavity formed by the closed cups. Holes 12 are commonly provided in the cups 15 and 16 to permit fluid to drain from the cups.

As explained above, the tissue sample can be difficult to dislodge from its position in or between the cups 15 and 16, and a small implement, such as a needle, must be manually applied by medical personnel to pry the sample from the distal end. Where such holes 12 are provided, medical personnel will insert a small implement through hole 12 to aid in dislodging the sample from the cups.

Figure 2:
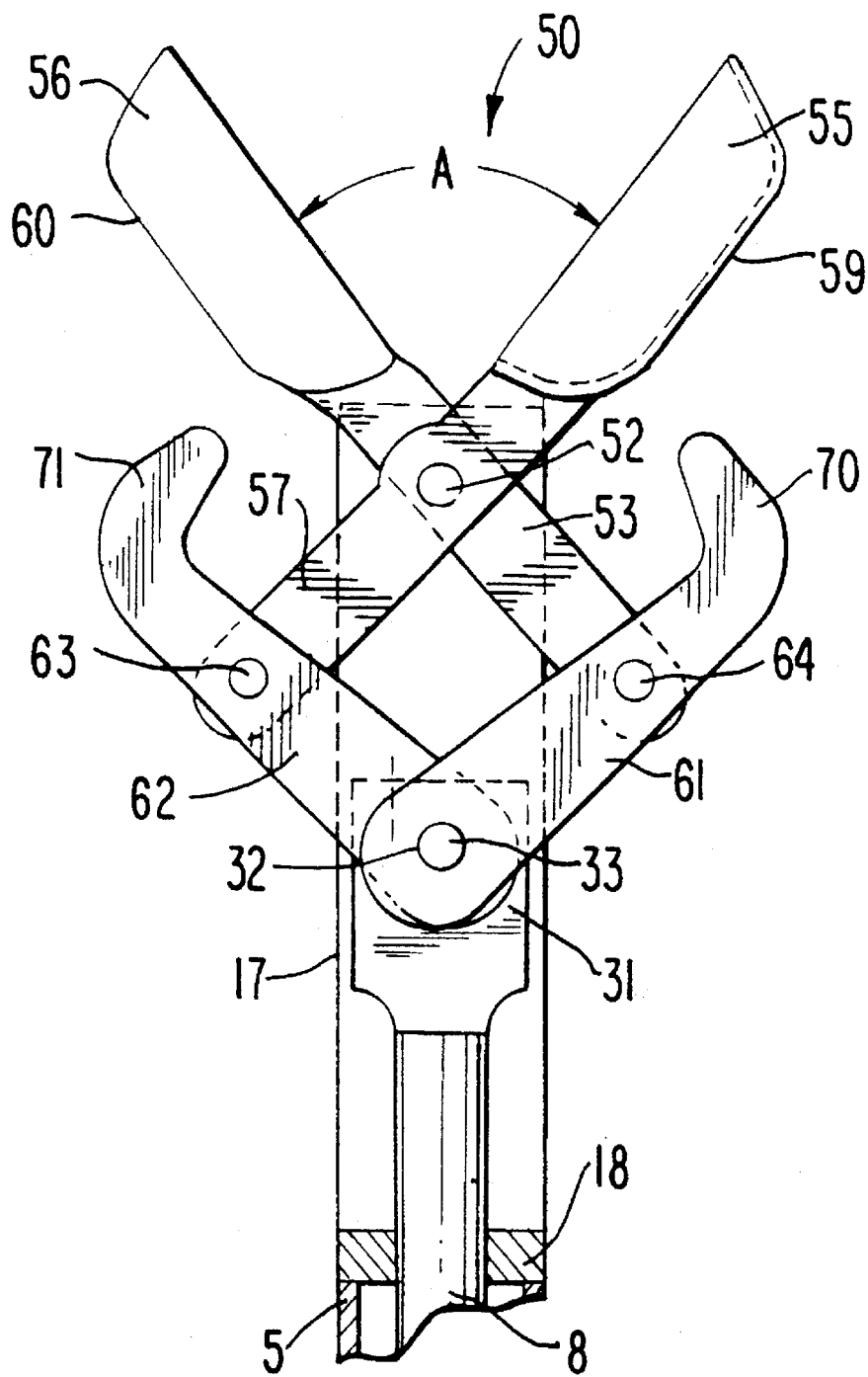
FIG. 2 is a partial sectional elevation view of one preferred embodiment of the forceps of the invention, in a partially opened position.
Figure 3:
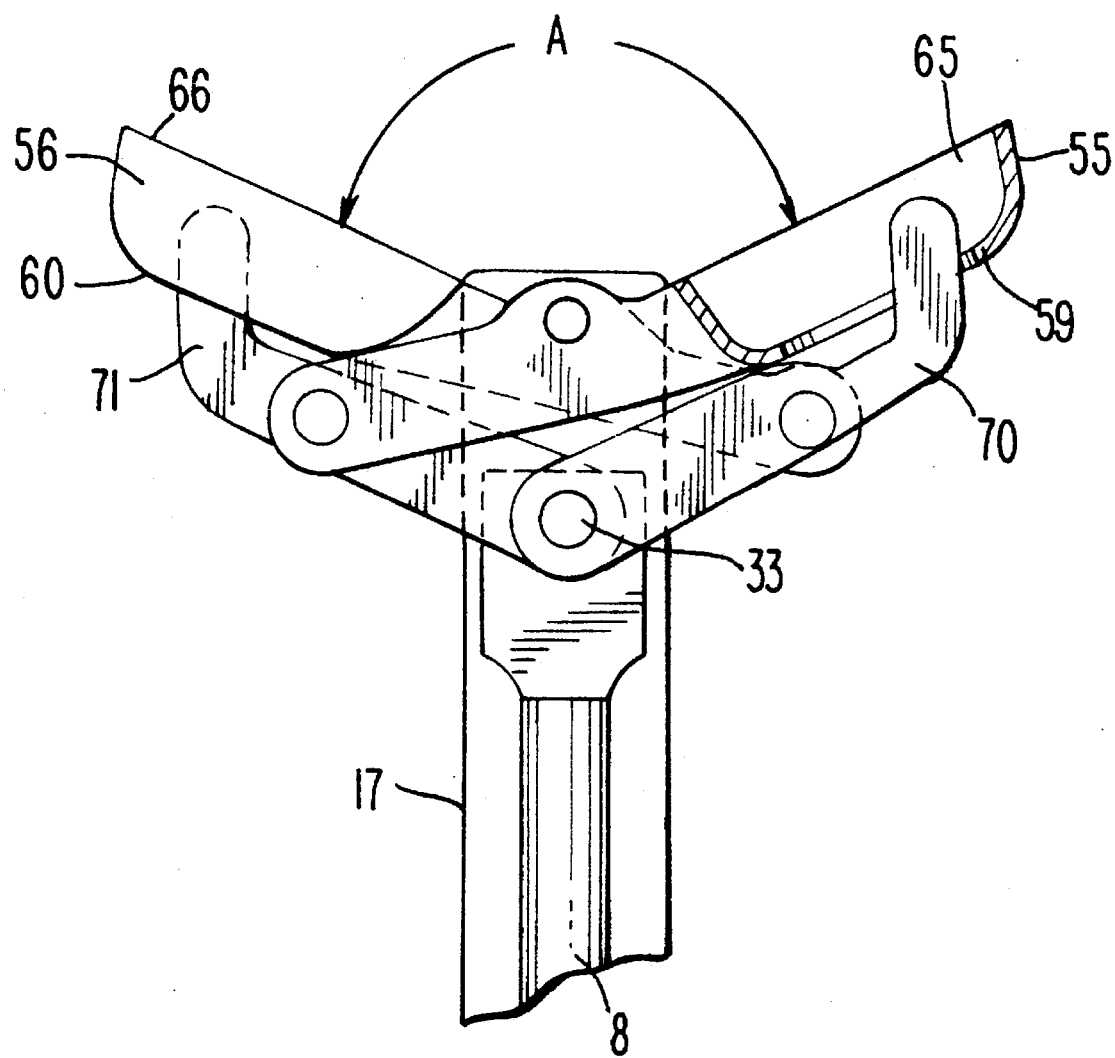
FIG. 3 is a partial sectional view of the forceps of FIG. 2, in a fully open position.
Figure 4:
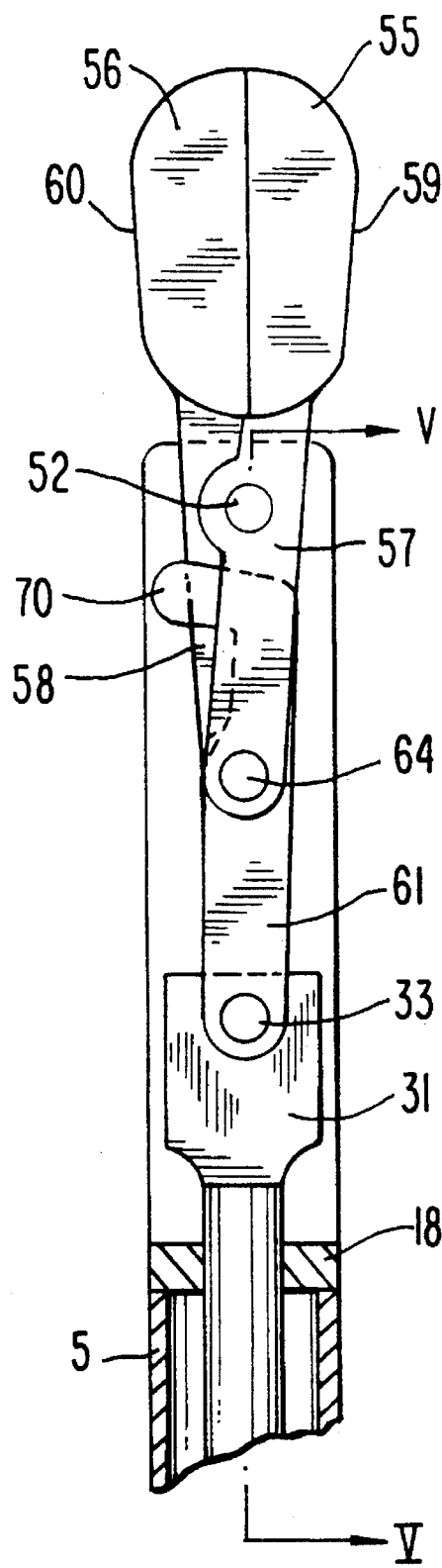
FIG. 4 is a partial sectional view of the forceps of FIG. 2, in a fully closed position.

A preferred embodiment of the improved tissue sample ejection means 50 of the invention for use in biopsy forceps is shown in FIGS. 2–4. The forceps is shown with the cups 55 and 56 partially opened in FIG. 2. The actuating wire 8 is slidably disposed within the hollow cable 5, which is shown in cross-section. A clevis 17 (also shown in cross-section) is rigidly attached to the cable 5 at joint 18, as by brazing or welding.

The wire 8 has a flattened distal end 31 with a hole 32. Two scissor links 61 and 62 are pivotally attached at their proximal ends to the flattened end 31 of the wire by a pin 33 that extends through hole 32.

The cups 55 and 56 have integral levers 57 and 58, respectively, depending from their proximal edges. The levers 57 and 58 are pivotally attached near their centers to the clevis 17 by a pin 52. The cups 55 and 56 are thereby permitted to open and close in arcuate paths about pin 52. The cups are provided with ejection holes 59 and 60, for ejection of the tissue sample after the forceps are removed from the patient, as explained below.

The proximal ends of the levers 57 and 58 are pivotally attached to the distal ends of the scissor links 62 and 61, respectively, by pins 63 and 64, respectively. It will be understood that by sliding the wire 8 in the distal direction relative to the cable 5, the distance between the pivot pins 52 and 33 is reduced, toggling the pivot pins 63 and 64 outward. The resulting pivoting motion of the levers 57 and 58 opens the cups 55 and 56.

The scissor links 61 and 62 are further provided with ejection plungers 70 and 71 depending from the distal ends of the links. The ejection plungers are curved inward so that they are aligned with the holes 59 and 60, respectively, as the cups 55 and 56 are opened. When the cups are opened more than approximately 90°, as shown by angle A in FIG. 3, the distal ends of the ejection plungers 70 and 71 enter the ejection holes 59, 60. Further opening of the cups 55 and 56 results in the ejection plungers 70 and 71 protruding into the interiors 65 and 66 of the cups. A tissue sample lodged in one or the other of the cups 55 and 56 can thus be dislodged and deposited into an appropriate container for storage and shipment merely by movement of slide 21 in the distal direction to thereby move wire 8 in cable 5 until the ejection plungers 70 and 71 are forced through the ejection holes 59 and 60.

FIG. 4 shows the tissue sample collection means 50 with the cups 55 and 56 in a fully closed position. In the simplified illustration of FIG. 4, only one side of the scissors linkage and ejection plungers are shown in the interest of clarity. However, from this illustration, it will be apparent that both of the ejection plungers 70 and 71, which depend distally from scissor links 61 and 62, are disposed within the edges of the clevis 17 for smooth transport though the biopsy channel of the endoscope (not shown).

Figure 5:
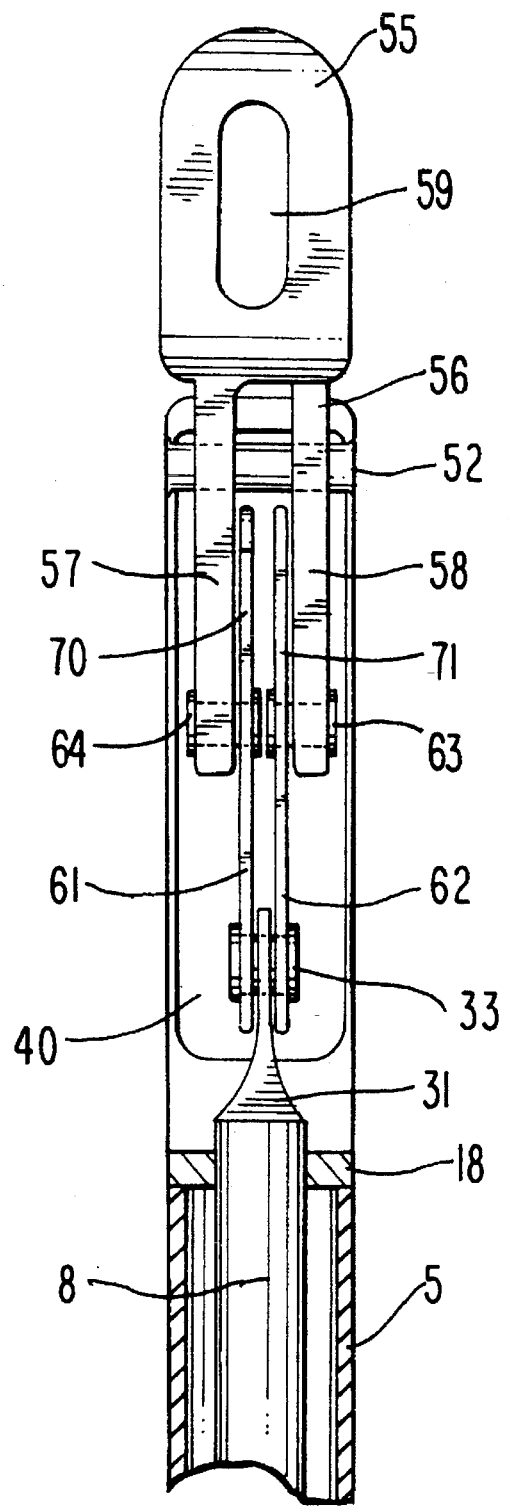
FIG. 5 is a partial sectional view of the forceps of FIG. 4 taken along line V—V.

The spatial relationship of the elements is fully shown in FIG. 5 which is a sectional view taken along section line V—V of the clevis 17 and cable 5 in FIG. 4. Clevis 17 is provided with a pair of openings 40 to permit the scissor linkages ejection plungers to extend outwardly during the operation. Levers 57 and 58 are offset from the axial centerline of cups 55 and 56. In this embodiment scissor linkages 61 and 62 with integral plungers 70 and 71, respectively, are positioned between levers 57 and 58, and pivot about pins 64 and 63. Other arrangements will be apparent to those skilled in the art for producing the required movement of the ejection plungers from the interior of the clevis 17 to the interior of the cups 55 and 56 when the latter are moved to the fully opened position for discharge of the tissue specimen.

Figure 6:
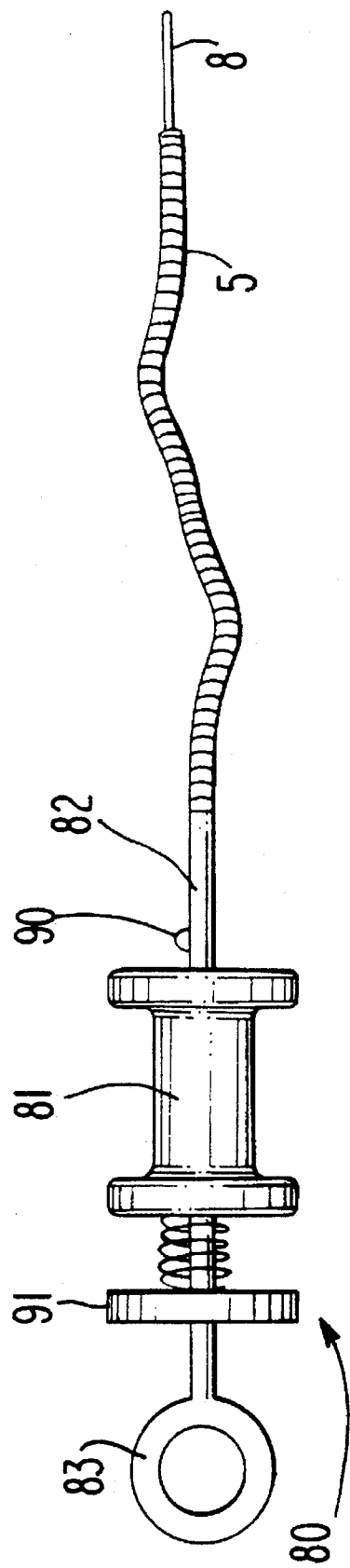
FIG. 6 is a partial view of the proximal end of one preferred embodiment of the invention.

Shown in FIG. 6 is a preferred actuation means 80 for use with the biopsy ejection forceps of the invention. A spool 81 is slidably mounted on a shaft 82 with a grip 83 depending from its proximal end. The cable 5 is mounted to the shaft 82. The wire 8 is operably attached to the spool 81, so that a sliding movement of the spool 81 on the shaft 82 will produce a similar movement of the wire 8 within the cable 5, thus opening and closing the cups as described above in connection with FIGS. 2–4.

The travel of the spool 81 along the shaft 82 in the distal direction is limited by the latch 90. In this preferred embodiment, the position on the shaft 82 at which the spool 81 abuts the latch 90 corresponds to he position of the tissue sample collection means wherein the cups are opened to an angle of approximately 90°. This cup position is used by the surgeon during the operative procedure to place the cups over the tissue sample to be removed. The surgeon then slides the spool 81 in the proximal direction, away from the latch 90, to close the cups.

An ejection actuator plate 91 is slidably mounted on the shaft 82 on the proximal side of the spool 81. The ejection actuator plate 91 is operably attached to the latch 90 such that a distal movement of the actuator plate 91 releases the latch 90. When the tissue sample is to be ejected from the cups 55 and 56, the ejection actuator plate is moved in the distal direction, first releasing the latch 90, and then contacting and moving the spool 81 until the tissue sample collection means reaches the position wherein the cups are opened to an angle of approximately 120°, the ejection plungers 70 and 71 enter cups 55 and 56, respectively, and the tissue sample is dislodged from the forceps.

Figure 7:
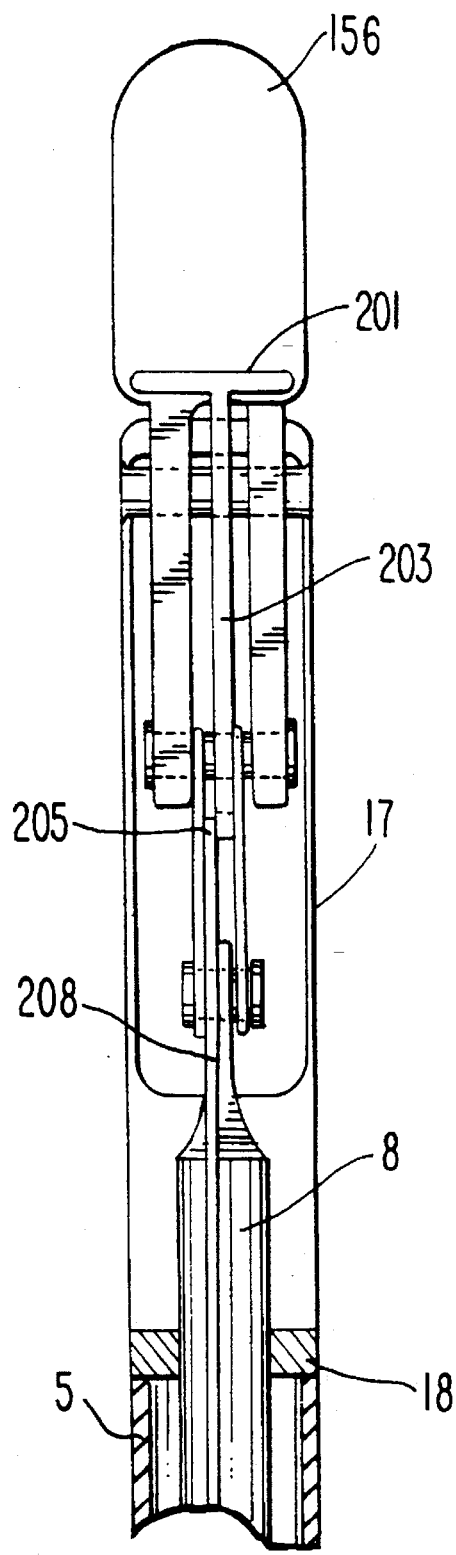
FIG. 7 is a plan view in partial section of the distal end of another embodiment of a biopsy ejection forceps of the invention in the closed position.
Figure 8A:
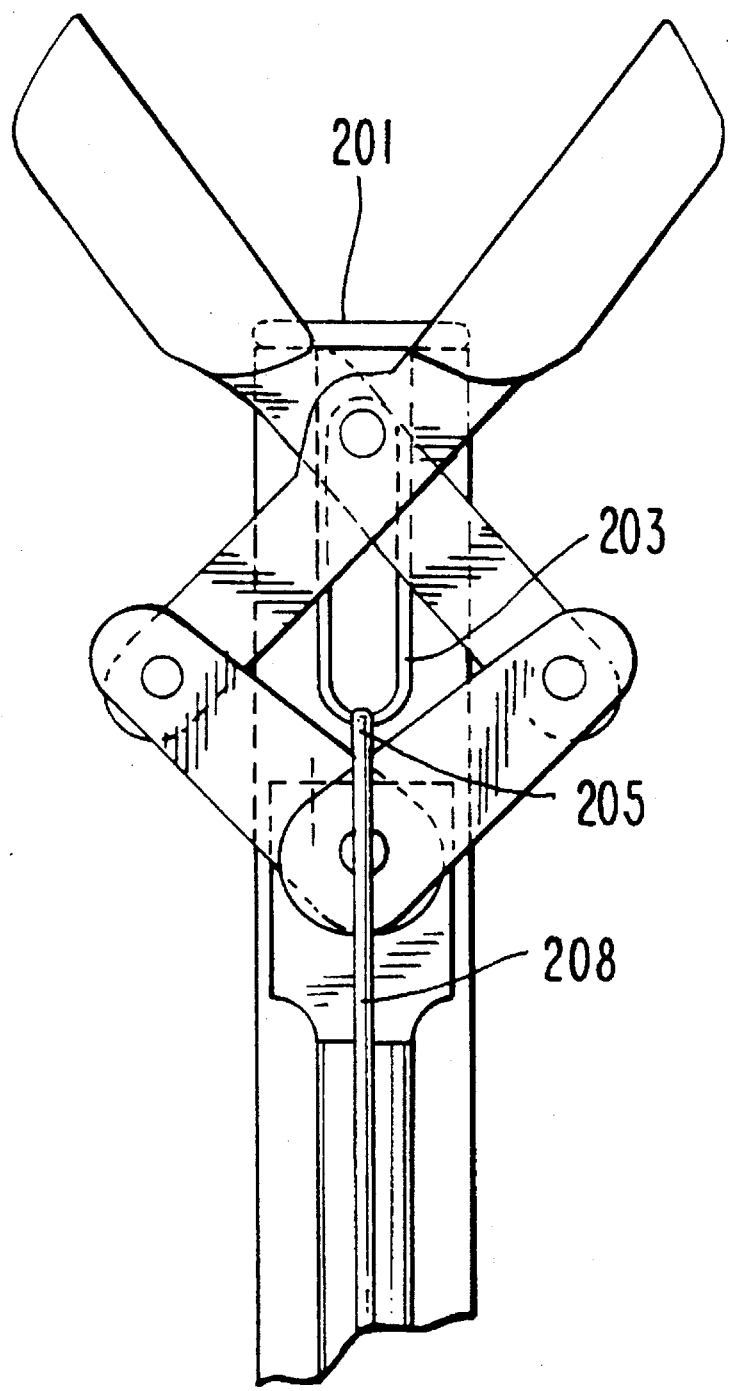
FIG. 8A is a side view in partial section of the forceps of FIG. 7, in an open position.
Figure 8B:
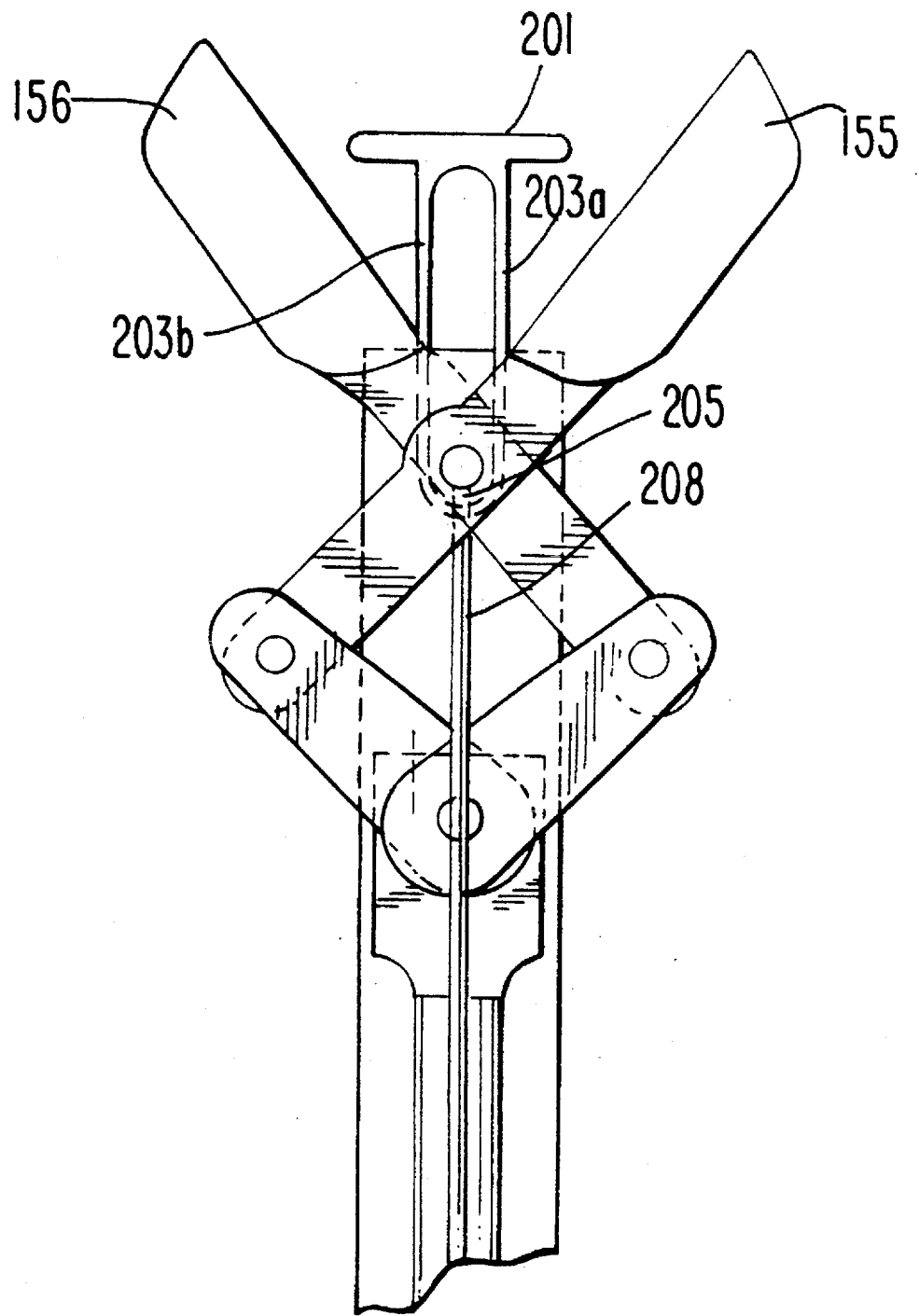
FIG. 8B is the same view as 8A in which the ejection means is extended.

A further embodiment of the invention is shown in FIGS. 7, 8A and 8B. In this embodiment, an ejector plate assembly 200 is attached to the distal end of a second wire 208 which is carried in flexible cable 5 adjacent and parallel to wire 8.

As shown in FIGS. 8A and 8B, the ejection plate 200 is generally T-shaped in cross section and comprises a generally circular or oval top member 201 that fits closely within the proximal end of the cups 155, 156 when they are in the closed position. Joined to, or formed integrally with the underside of top member 201 is leg member 203, which in this embodiment is comprised of a pair of spaced apart elements 203a and 203b, joined at their proximal ends.

Wire 208 is secured to the proximal end of leg 203 at 205. The proximal end of wire 208 is secured to manual actuator means at the proximal end of the flexible cable 5. The ejection plate actuator means can comprise a separate finger or thumb grip having the configuration of thumb grip 83 shown in FIG. 5. Alternatively, wire 208 can be slidably affixed to spool 81 so that wire 208 is advanced in the distal direction only after the cups 155 and 156 have been fully opened and the release mechanism 91 has been activated.

The wire 208 with the ejection plate 201 and hole 200 can be used in conjunction with the prior art mechanism described in connection with FIG. 1 for opening and closing the cups 155 and 156. A distal movement of the wire 208 moves the plate 201 in a distal direction, as shown in FIG. 8B. A tissue sample contained within the cups is ejected distally by the plate 201.

As will be apparent to one skilled in the art, those elements which are described as having been formed from the flattened end of the wire, and therefore integral with the wire, can also be fabricated as a separate element and thereafter welded or otherwise secured to the end of the wire.

Other configurations of the ejection biopsy forceps within the scope of the invention, such as additional combinations of the embodiments shown, will be apparent to one skilled in the art.

We claim:

1. A biopsy forceps for retrieving a tissue sample from an organ, comprising:

a flexible, hollow cable with a proximal end and a distal end;

a plurality of opposing cups pivotally attached to said distal end of said hollow cable for severing the tissue sample from the organ;

a first wire slidably disposed within said hollow cable and operably connected to said cups;

a second wire slidably disposed within said hollow cable;

tissue sample ejecting means operably attached to said second wire for ejecting the tissue sample from said cups;

first means on said proximal end of said cable for moving said first wire from a first position whereby said cups are closed to a second position whereby said cups are opened;

second means on said proximal end of said cable for sliding said second wire to activate said tissue sample ejecting means.

2. A biopsy forceps for retrieving a tissue sample from an organ, comprising:

a flexible, hollow cable with a proximal end and a distal end;

a plurality of opposing cups pivotally attached to said distal end of said hollow cable for severing the tissue sample from the organ;

tissue sample ejection means disposed in a proximal end of said cups;

a first wire slidably disposed within said hollow cable and operably connected to said cups whereby sliding said wire opens and closes said cups;

a second wire slidably disposed within said hollow cable and connected to said tissue sample ejection means whereby sliding said second wire moves said tissue sample ejection means between said cups, ejecting the tissue sample from the cups.

3. The biopsy forceps of claim 2, wherein said tissue sample ejection means comprises an ejection plate and a leg member.

4. The biopsy forceps of claim 3, wherein said leg member comprises a pair of spaced apart elements joined at their proximal ends.

5. The biopsy forceps of claim 2, wherein said first wire has a flattened area with a transverse hole for engaging an operating pin operably connected to said opposing cups.

6. A biopsy forceps for retrieving a tissue sample from an organ, comprising:

a flexible, hollow cable with a proximal end and a distal end;

first and second opposing cups pivotally attached to said distal end of said hollow cable for severing the tissue sample from the organ, said opposing cups each having an ejection aperture;

first and second scissor links pivotally attached respectively to said first and second opposing cups;

a wire slidably disposed within said hollow cable having a distal end pivotally attached to said scissor links, whereby a movement of said wire in said cable in the distal direction toggles said scissor links and opens said cups;

ejection plungers rigidly attached to said scissor links and positioned to protrude through said ejection apertures when said cups are opened.

7. The biopsy forceps of claim 6 wherein the ejection plungers are curved.

8. The biopsy forceps of claim 6 wherein the ejection plunger is formed integrally with the scissor link.

9. The biopsy forceps of claim 6 wherein the ejection plungers are moved from a first position adjacent the wire when the cups are in a closed position through an arcuate path when the cups are opened.

10. The biopsy forceps of claim 6 wherein the ejection plungers are radially disposed within the periphery of the outer surfaces of the closed cups.

11. In a biopsy forceps having a flexible cable with proximal and distal ends, a plurality of opposing cups on the distal end of the cable for severing and retrieving a tissue sample, a wire slidably disposed within the cable and operably attached to the opposing cups, and means for sliding the wire mounted on the proximal end of the cable, the improvement comprising ejection means for ejecting the tissue sample from the opposing cups, where said ejection means is operably attached to the wire and said ejection means extends into the interior of the cups.

12. The biopsy forceps of claim 11, wherein the ejection means for ejecting the tissue sample comprises pushing means for pushing the tissue sample from the cups, said pushing means being mounted on a distal end of the wire.

13. The biopsy forceps of claim 12, wherein the pushing means comprises a plate.

14. The biopsy forceps of claim 11 wherein said ejection means comprises at least one ejection plunger for protruding through a hole in at least one of said opposing cups.

15. The biopsy forceps of claim 11 further comprising a means on said proximal end of said cable for sliding said wire within said cable; said sliding means including a latch for selectively preventing movement between a position for opening the cups to retrieve a tissue sample and a position for ejecting the tissue sample.

* * * * *